United States Patent

Glamkowski et al.

[11] 4,192,874
[45] Mar. 11, 1980

[54] SUBSTITUTED 1,2,6,7-TETRAHYDROINDOLO[1,7-AB][1,5]BENZODIAZEPINES

[75] Inventors: Edward J. Glamkowski, Warren; James M. Fortunato, Somerville, both of N.J.

[73] Assignee: American Hoechst Corporation, Bridgewater, N.J.

[21] Appl. No.: 956,903

[22] Filed: Nov. 2, 1978

[51] Int. Cl.² .................... A61K 31/55; C07D 487/04
[52] U.S. Cl. ........................... 424/248.54; 260/243.3; 260/244.4; 260/326.31; 260/326.81; 260/326.9; 424/248.56; 424/232; 424/250; 424/267; 424/274
[58] Field of Search ............... 260/326.1, 326.9, 243.3, 260/244.4, 326.31, 326.81; 424/274, 250, 267, 248.54, 248.56

[56] References Cited

U.S. PATENT DOCUMENTS 3,732,212 5/1973 Carabateas .................. 260/243.3
4,013,679 3/1977 Riva et al. ..................... 424/274

Primary Examiner—Alton D. Rollins
Assistant Examiner—M. C. Eakin
Attorney, Agent, or Firm—Curtis, Morris & Safford

[57] ABSTRACT

What is disclosed are 1,2,6,7-tetrahydroindolo[1,7-ab][1,5]benzodiazepines of the formula

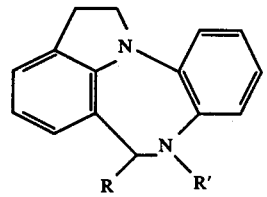

wherein
R is hydrogen, loweralkyl, or cycloalkyl;

R' is

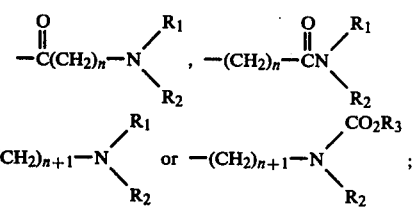

n is an integer from 1 to 3;
$R_1$ is hydrogen, loweralkyl, or phenylloweralkyl;
$R_2$ is hydrogen or loweralkyl;
or $R_1$ and $R_2$ may be taken together with the nitrogen to which they are attached to form pyrrolidinyl, piperidino, morpholino, or phenylpiperazinyl; and
$R_3$ is loweralkyl; and the pharmaceutically acceptable acid addition salts thereof.

These compounds are useful as antidepressants and as analgesic and anti-inflammatory agents.

31 Claims, No Drawings

SUBSTITUTED 1,2,6,7-TETRAHYDROINDOLO[1,7-AB][1,5]BENZODIAZEPINES

This invention relates to novel 1,2,6,7-tetrahydroindolo [1,7-ab] [1,5] benzodiazepines and to their physiologically tolerable acid addition salts which are useful as antidepressant, analgesic and antiinflammatory agents, to methods of treatment with pharmaceutically effective amounts thereof, and to pharmaceutical compositions containing such compounds as essential active ingredients.

To the best of our knowledge, the compounds of this invention have not heretofore been described or suggested. Riva et al., in U.S. Pat. No. 4,013,679 disclose compounds of the formula

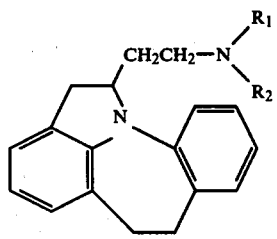

which are reported to possess antidepressant activity. But these compounds are substantially different from those of the present invention.

The compounds of the present invention may be depicted by the general formula

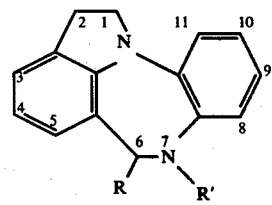

wherein
R is hydrogen, lower alkyl, or cycloalkyl;
R' is

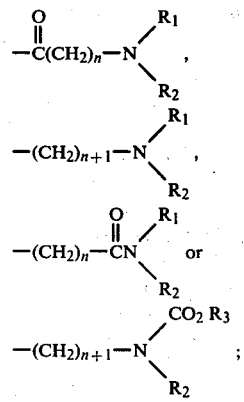

n is an integer from 1 to 3;
$R_1$ is hydrogen, lower alkyl, or phenyl lower alkyl;
$R_2$ is hydrogen or lower alkyl;
or $R_1$ and $R_2$ may be taken together with the nitrogen to which they are attached to form pyrrolidinyl, piperidino, morpholino, or phenyl piperazinyl;
$R_3$ is lower alkyl; and the pharmaceutically acceptable acid addition salts thereof.

In the above definitions, lower alkyl means those radicals having 1 to 4 carbon atoms and cycloalkyl embraces those radicals having 3 to 6 carbon atoms.

As to the physiologically acceptable salts, those coming within the purview of this invention include pharmaceutically acceptable acid-addition salts. Acids useful for preparing these acid-addition salts include, inter alia, inorganic acids such as the hydrohalic acids (e.g., hydrochloric and hydrobromic acid), sulfuric acid, nitric acid, phosphoric acid and perchloric acid, and organic acids such as oxalic, malonic, succinic, maleic, fumaric, tartaric, citric, acetic, benzoic, salicylic, ascorbic, etc.

The compounds of the present invention may be prepared by several methods of preparation. For example, compounds wherein R' is

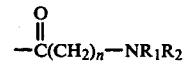

may be prepared by reacting the corresponding haloacyl derivative

with the appropriate amine in a conventional manner. The haloacyl derivative may be prepared by treating the starting material [R'=H] for this invention with a halogenated acid halide

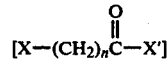

and a mild base such as sodium bicarbonate or triethylamine. Synthesis of the starting material is illustrated in Example 1.

Compounds wherein R' is —$(CH_2)_{n+1}$—$NR_1R_2$ may be obtained by reducing the above aminoacyl derivative

in a conventional manner, for example with $LiAlH_4$ or $BH_3$.

Alternatively, an appropriate nitrile derivative [R'=—$(CH_2)_n$—CN] may be reduced, for example with $LiAlH_4$, to yield the desired unsubstituted aminoalkyl compound [R" —$(CH_2)_{n+1}$—$NH_2$]. The nitrile derivative may be prepared in any conventional manner such as, for instance, treating the starting material [R'=H] with a haloaliphatic nitrile [X—$(CH_2)_n$—CN]. The unsubstituted aminoalkyl compound may then be reacted with an alkyl chloroformate [Cl—$CO_2$—$R_3$] to yield the corresponding carbamate derivative [R'=—$(CH_2)_n$$NHCO_2$—Alk] which may then be reduced with $LiAlH_4$ to the corresponding methylaminoalkyl compound [R'=—$(CH_2)_n$$NHCH_3$]

The aminoalkyl compounds may additionally be derived from the corresponding methanesulfonate derivative [$R'=-(CH_2)_{n+1}-OSO_2CH_3$] by reacting said derivative with the desired amine [$HNR_1R_2$]. The methanesulfonate derivative may be synthesized in any conventional manner. For example, the starting material [$R'=H$] may be converted to an ester derivative [$R'=-(CH_2)_nCO_2-R_3$] by treatment with an appropriate halogenated ester [$X-(CH_2)_nCO_2-R_3$] or acrylate [$CH_2=CHCO_2-R_3$], and said ester derivative may be reduced to the corresponding alcohol [$R'=-(CH_2)_{n+1}-OH$]. This alcohol may then be treated with methanesulfonyl chloride to yield the methanesulfonate derivative.

Compounds wherein R' is

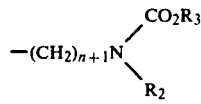

may be obtained by reacting an aminoalkyl compound [$R'=-(CH_2)_{n+1}-NHR_2$] as derived above with an alkyl chloroformate [$Cl-CO_2-R_3$] using conventional methods.

And compounds wherein R' is

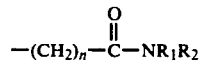

may be prepared from the above described ester derivatives [$R'=-(CH_2)_n\ CO_2-R_3$] by treatment with an appropriate amine [$HNR_1R_2$]. These amides may also be reduced, for example with LiAlH$_4$, to the corresponding aminoalkyl compound [$R'=-(CH_2)_{n+1}-NR_1R_2$].

The compounds of the present invention are useful in the treatment of depression in mammals as demonstrated by their ability to inhibit tetrabenazine-induced depression in mice [International Journal of Neuropharmacology 8, 73 (1969)], standard assay for useful antidepressant properties. Thus, for example, 6-methyl-7-(methylaminoacetyl)-1,2,6,7-tetrahydroindolo [1,7-ab] [1,5] benzodiazepine and 7-(2-aminoethyl)-6-methyl-1,2,6,7-tetrahydroindolo [1,7-ab] [1,5] benzodiazepine dihydrobromide at oral doses of 2.0 and 2.2 mg/kg of body weight, respectively, demonstrate a 50% inhibition of ptosis of tetrabenazine-induced depression in mice.

The compounds of this invention are additionally useful as anti-inflammatory agents due to their ability to suppress inflammation in mammals. This activity is demonstrated in the carrageenin induced rat paw edema anti-inflammatory assay [Proc. Soc. Exptl. Biol. Med., 111, 544 (1962); J. Pharmacol. Exp. Ther., 141, 369 (1963)]. For example, under this test 6-methyl-7-(N,N-dimethyl-3-aminopropionyl)-1,2,6,7-tetrahydroindolo[1,7-ab] [1,5]-benzodiazepine exhibits a 50% inhibition of edema at an oral dose of 6.48 mg/kg of body weight. Topical anti-inflammatory activity is also exhibited by the instant compounds. For example, 6-methyl-7-(3-piperidinopropionyl)-1,2,6,7-tetrahydroindolo[1,7-ab] [1,5]-benzodiazepine demonstrates a 50% reduction of oxazolone induced mouse ear edema [Br. Journal of Pharmacol., 43, 403–408 (1971)] at an application of 0.068 mg per ear.

The compounds of the present invention are still further useful as analgesic agents due to their ability to alleviate pain in mammals as demonstrated in the 2-phenyl-1,4-benzoquinone-induced writhing test in mice, a standard assay for analgesia [Proc. Soc. Exptl. Biol. Med., 95, 729 (1957)]. Thus, for instance, an approximately 50% inhibition of writhing is effected by 2.3 mg/kg of body weight of 7-(N,N-dimethyl-3-aminopropyl)-1,2,6,7-tetrahydroindolo[1,7-ab] [1,5]benzodiazepine dihydrochloride administered subcutaneously.

These compounds are useful as any of the above three categories of pharmaceutical agents when administered in an amount ranging from about 0.1 to 100 mg per Kg of body weight per day.

Some compounds within the scope of this invention have greater pharmaceutical activity than others. Some of the latter, such as those in which

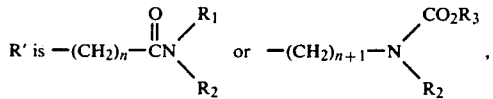

are nevertheless desirable as intermediates for the preparation of more active compounds.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like, a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for examples, as coatings. Thus, tablets or pills may be coated with sugar, shellac, or other enteric coating agents. A syrup may contain in addition to the active compounds, sucrose as a sweetening agent, and certain preservatives, dyes and colorings and flavors. Materials used in preparing these various compositions should be pharmaceutically pure and non-toxic in the amounts used. For the purpose of parenteral therapeutic administration, the active compounds of the invention may be incorporated into a solution or suspension. These preparations should contain at least 0.1% of active compound, but may be varied to between 0.5 and about 50% of the weight thereof. The amount of active compounds in such compositions is such that a suitable dosage will be obtained.

Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For the purpose of topical application, the compounds of this invention may be incorporated into a solution, suspension, ointment, cream or salve. These preparations should contain at least 0.01% of the active compound but may be varied to between 0.05 and about 20% of the weight thereof. The amount of active compound in such compositions is such that a suitable dosage will be obtained. Preferred compositions for the treatment of dermal inflammations are those containing between 0.1 and 10% of the active compound.

The topical compositions may also include the following components: water, fixed oils, polyethylene glycols, glycerol, petroleum, stearic acid, beeswax, other synthetic solvents or mixtures thereof; antibacterial agents such as benzyl alcohol or methyl paraben; antioxidants such as α-toco-pherol acetate; chelating agents such as ethylenediaminetetracetic acid; buffers such as acetates, citrates or phosphates; emulsifying agents such as polyoxyethylene monobleate and coloring materials and adjuvants such as ferric oxide or talc. The topical preparations can be enclosed in tubes, bottles or jars made of metal, glass or plastic.

This invention is further illustrated by the following examples:

EXAMPLE 1

Starting materials for use in preparing the compounds of the present invention may be synthesized according to the reaction scheme depicted below. This synthesis is more fully described by Glamkowski et al. in concurrently filed U.S. patent application Ser. No. 956,904, entitled "Indolo, 1,2-dihydroindolo, and 1,2,6,7-tetrahydroindolo[1,7-ab] [1,5]benzodiazepines." As can be seen, the R-substituent in the ultimate starting material (I) may be varied by selecting an appropriately substituted carbonyl chloride to be reacted with the 1-(o-aminophenyl)indoline. For example, acetyl chloride will yield R=CH₃ (IB), while cyclohexanecarbonyl chloride will yield

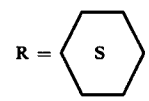

(IC).

R will be hydrogen (IA) if formic acid is employed.

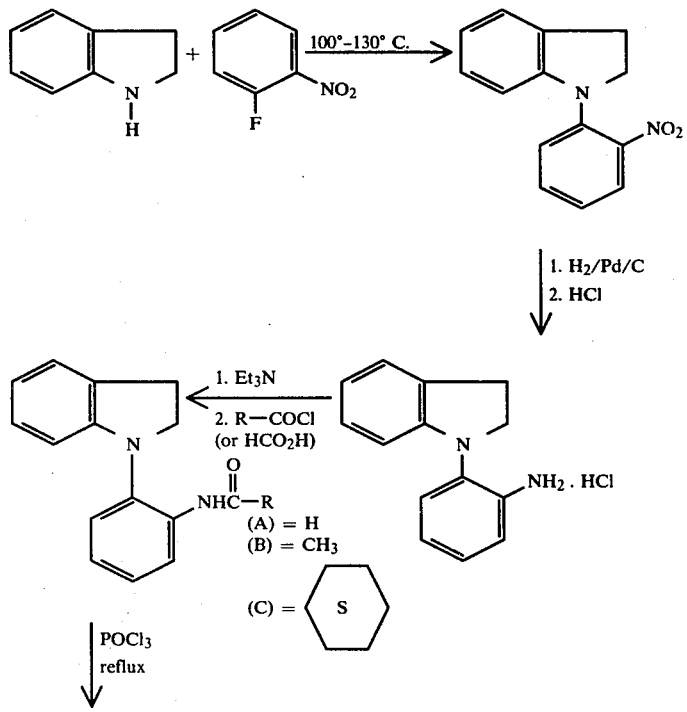

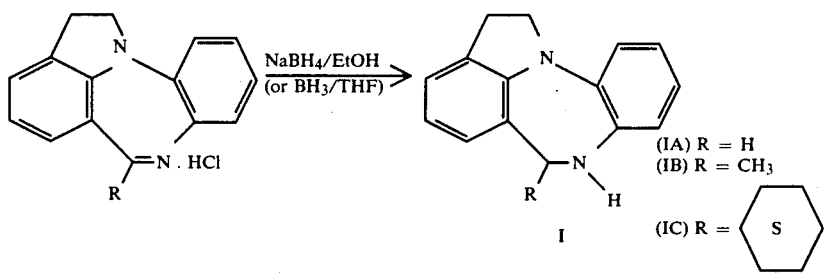

(IA) R = H
(IB) R = CH₃
(IC) R = [cyclohexyl-S group]

EXAMPLE II

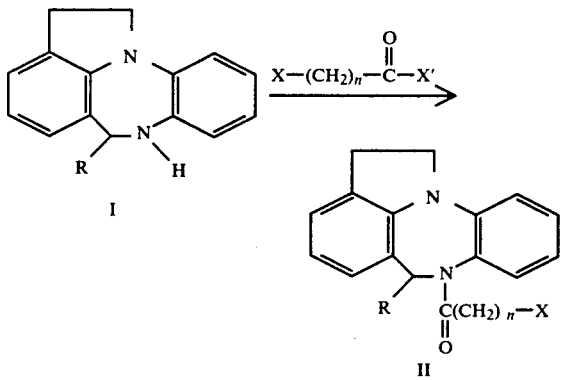

IIA. 7-Bromoacetyl-1,2,6,7-tetrahydroindolo [1,7-ab] [1,5] benzodiazepine

A stirred mixture, under nitrogen, of 17.8 g of IA and 25.2 g of powdered sodium bicarbonate in 250 ml of methylene chloride is cooled to 0° C. and treated dropwise with a solution of 24.2 g of bromoacetyl bromide in 50 ml of methylene chloride. The addition is at such a rate (1.5 hours) as to maintain the temperature below 5° C. The reaction mixture is stirred an additional 2 hours at 0° C., then at room temperature 18 hours. Water is added and the organic phase is separated, washed with 3 N—NaOH and water, dried over sodium sulfate, and concentrated to a solid. The solid is digested with 20 ml of absolute ethanol and after stirring at room temperature 1 hour, granular crystals of 7-bromoacetyl-1,2,6,7-tetrahydroindolo [1,7-ab] [1,5] benzodiazepine are collected, m.p. 132°–136° C.

IIB. 7-Bromoacetyl-6-methyl-1,2,6,7-tetrahydroindolo [1,7-ab] [1,5] benzodiazepine The procedure of Example IIA is repeated with 7.09 g of IIB (in 50 ml methylene chloride and 8.40 g sodium bicarbonate) and 8.08 g of bromoacetyl bromide (in 25 ml methylene chloride). The organic phase is washed with 3 N—HCl and then with water, dried over sodium sulfate, concentrated to an oil, and recrystallized twice from ethanol to furnish 7-bromoacetyl-6-methyl-1,2,6,7-tetrahydroindolo [1,7-ab] [1,5] benzodiazepine, m.p. 123°–125° C.

IIC. 7-(3-Bromopropionyl)-6-methyl-1,2,6,7-tetrahydroindolo [1,7-ab] [1,5] benzodiazepine The procedure of Example IIA is repeated with 16.5 g of IB (in 200 ml methylene chloride and 22.7 g sodium bicarbonate) and 15.4 g of 3-bromopropionyl chloride (in 50 ml methylene chloride). The organic phase is washed with 3 N—HCl, 3 N—NaOH and water, dried over sodium sulfate, concentrated to an oil, boiled and triturated with 100 ml hexane, filtered, washed with hexane, dried, and recrystallized from methanol to yield 7-(3-bromopropionyl)-6-methyl-1,2,6,7-tetrahydroindolo [1,7-ab] [1,5] benzodiazepine, m.p. 149°–151° C.

IID. 7-(3-Bromopropionyl)-1,2,6,7-tetrahydroindolo [1,7-ab] [1,5] benzodiazepine The procedure of Example IIA is repeated with 17.63 g of IA (in 100 ml chloroform and 12.1 g potassium carbonate) and 0.0874 mole of 3-bromopropionyl chloride (in 20 ml chloroform) except that the mixture is stirred for 1.5 hours at room temperature after the addition. The organic phase, after addition of water, is separated and washed with water, dried of sodium sulfate, filtered, concentrated, recrystallized from ethanol, purified by dry column chromatography, and is recrystallized from ethanol, then isopropyl ether or yield 7-(3-bromopropionyl)-1,2,6,7-tetrahydroindolo [1,7-ab] [1,5] benzodiazepine, m.p. 120°–121.5° C.

IIE. 7-(4-Chlorobutyryl)-6-methyl-1,2,6,7-tetrahydroindolo [1,7-ab] [1,5] benzodiazepine The procedure of Example IIA is repeated with 14.1 g of IB (in 200 ml of methylene chloride and 20.2 g sodium bicarbonate) and 11.2 g of chlorobutyryl chloride (in 50 ml methylene chloride). The organic phase is washed with 3 N—HCl, 3 N—NaOH and water, dried over sodium sulfate, concentrated to an oil, crystallized from ethanol, washed with ethanol, dried, and recrystallized from methanol, to yield 7-(4-chlorobutyryl)-6-methyl-1,2,6,7-tetrahydroindolo [1,7-ab] [1,5] benzodiazepine, m.p. 88°–90° C.

IIF. 7-(3-Bromopropionyl)-6-cyclohexyl-1,2,6,7-tetrahydroindolo [1,7-ab] [1,5] benzodiazepine The procedure of Example IIA is repeated with 15.3 g of IC (in 175 ml methylene chloride and 8.5 ml triethylamine) and 0.06 mole 3-bromopropionyl chloride (in 22 ml methylene chloride). After stirring 2.5 hours at room temperature, the product is poured into water and the organic layer is washed with 4N-HCl, 10% NaOH, and brine, dried over sodium sulfate, and concentrated to yield 7-(3-bromopropionyl)-6-cyclohexyl-1,2,6,7-tetrahydroindolo [1,7-ab] [1,5] benzodiazepine.

EXAMPLE III

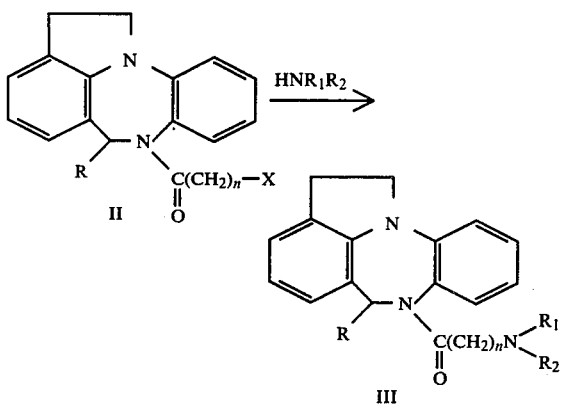

IIIA. 7-Methylaminoacetyl-1,2,6,7-tetrahydroindolo [1,7-ab] [1,5] benzodiazepine Into 200 ml of absolute methanol, stirred and kept at 0°–5° C., is passed gaseous monomethylamine until saturated. To this is added 13.7 g of IIA in small portions. After 1 hour more at low temperature, and 3 hours at room temperature, the solution is boiled with charcoal, filtered, and concentrated. The residue is partitioned between chloroform and water. The organic phase is separated, washed further with water, with 3N–NaOH, again with water, dried over $Na_2SO_4$, and concentrated in vacuo. This material is column chromatographed and pure fractions are combined and concentrated. The concentrate is dissolved in 30 ml of boiling ethyl acetate, charcoaled, filtered and allowed to cool, and then filtered again. The filtrate is concentrated to yield 7-methylaminoacetyl-1,2,6,7-tetrahydroindolo [1,7-ab] [1,5] benzodiazepine, m.p. 128°–130° C.

Analysis: Calculated for $C_{18}H_{19}N_3O$: 73.70%C; 6.53%H; 14.32%N. Found: 73.56%C; 6.84%H; 14.54%N.

IIIB. 7-Dimethylaminoacetyl-1,2,6,7-tetrahydroindolo [1,7-ab] [1,5] benzodiazepine Into a stirred slurry of 10.3 g of IIA in 100 ml of absolute ethanol is passed gaseous dimethylamine, at a rate whereby the reaction temperature rises to 38° C. over a 15 minute period. The resultant reaction solution is concentrated to an oil which is extracted into 200 ml of chloroform. This organic phase is washed with water, 3N–NaOH, and water, dried over $Na_2SO_4$ and concentrated to an oil. The oil is boiled and scratched in 50 ml of hexane which induces crystallization of 7-dimethylaminoacetyl-1,2,6,7-tetrahydroindolo [1,7-ab] [1,5] benzodiazepine, m.p. 104°–107° C.

Analysis: Calculated for $C_{19}H_{21}N_3O$: 74.24%C; 6.89%H; 13.67%N. Found: 74.16%C; 6.81%H; 13.51%N.

IIIC. 7-(N,N-dimethyl-3-aminopropionyl)-1,2,6,7-tetrahydroindolo [1,7-ab] [1,5] benzodiazepine A rapidly stirred slurry of 16.0 g of IID in 100 ml absolute ethanol is heated to reflux while bubbling in dimethylamine gas. Reflux is maintained for 0.5 hours. The resulting solution is permitted to cool to room temperature, stirred with a small portion of charcoal, filtered and concentrated. The residue is dissolved in $CHCl_3$, washed with water and brine, dried ($Na_2SO_4$), filtered and concentrated. Column chromatography (silica gel/$Et_2O$—MeOH) of the resultant solid yields 7-(N,N-dimethyl-3-aminopropionyl)-1,2,6,7-tetrahydroindolo [1,7-ab] [1,5] benzodiazepine, m.p. 91.0°–92.5° C.

Analysis: Calculated for $C_{20}H_{23}N_3O$: 74.74%C; 7.21%H; 13.07%N. Found: 74.50%C; 7.25%H; 13.08%N.

IIID. 6-Cyclohexyl-7-(N,N-dimethyl-3-aminopropionyl)-1,2,6,7-tetrahydroindolo [1,7-ab] [1,5] benzodiazepine hydrochloride A stirred slurry of 5.00 g of the mixture of IIF in 100 ml absolute ethanol is brought to reflux while bubbling in gaseous dimethylamine. After 15 minutes at reflux, the product is permitted to cool to room temperature and concentrated. The resulting oil is dissolved in 100 ml of $CHCl_3$ and washed with water and brine, dried over $Na_2SO_4$, and concentrated to afford an oil. The free amine is dissolved in 50 ml absolute ethanol, filtered, cooled to 0° C. and treated with 50 ml ethereal HCl. The resulting salt is collected, dried, and recrystalized from ethanol-hexane to yield 6-cyclohexyl-7-(N,N-dimethyl-3-aminopropionyl)-1,2,6,7-tetrahydroindolo [1,7-ab] [1,5] benzodiazepine hydrochloride, m.p. 211°–214° C.

Analysis: Calculated for $C_{26}H_{33}N_2O \cdot HCl$: 70.97%C; 7.79%H; 9.55%N. Found: 71.32%C; 8.02%H; 9.82%N.

IIIE. 6-Methyl-7-methylaminoacetyl-1,2,6,7-tetrahydroindolo [1,7-ab] [1,5] benzodiazepine Into 200 ml of absolute methanol, stirred and kept at 0°–5° C., is passed gaseous monomethylamine until saturated. To this solution is added 17.9 g of IIB in small portions over a 1 hour period. The solution is then kept at 0° C. for 3 hours. The solution is then concentrated to a residue which is partitioned between chloroform and water. The organic phase is separated and washed further with water, with 3N—NaOH, again with water, dried over $Na_2SO_4$ and finally concentrated in vacuo to an oil. The oil is dissolved in 50 ml of chloroform and absorbed onto a column containing silica gel made up in benzene. After progressive elution with benzene, benzene-chloroform, and chloroform methanol mixtures, the product emerges with 2% methanol in chloroform. Pure fractions are combined and concentrated in vacuo to an oil which sets solid with crystals. The solid is triturated with 25 ml of ether to yield 6-methyl-7-methylaminoacetyl-1,2,6,7-tetrahydroindolo [1,7-ab] [1,5] benzodiazepine, m.p. 106°–110° C.

Analysis: Calculated for $C_{19}H_{21}N_3O$: 74.24%C; 6.89%H; 13.67%N. Found: 74.15%C; 6.71%H; 13.66%N.

IIIF. 7-Dimethylaminoacetyl-6-methyl-1,2,6,7-tetrahydroindolo [1,7-ab] [1,5] benzodiazepine Into a stirred slurry of 10.7 g of IIB in 100 ml of absolute ethanol is slowly passed a stream of gaseous dimethylamine. After 10 minutes, the reaction temperature reaches a maximum of 42° C. and a solution is obtained. The solution is concentrated and the residual oil is taken up in chloroform, washed with water, 3N—NaOH, and water, dried over $Na_2SO_4$ and concentrated to a thick oil. Trituration with 50 ml hexane affords 7-dimethylaminoacetyl-6-methyl-1,2,6,7-tetrahydroindolo [1,7-ab] [1,5] benzodiazepine, m.p. 104°–108° C.

Analysis: Calculated for: $C_{20}H_{23}N_3O$: 74.74%C; 7.21%H; 13.07%N. Found: 74.98%C; 7.34%H; 12.98%N.

IIIG.
6-Methyl-7-n-propylaminoacetyl-1,2,6,7-tetrahydroindolo [1,7-ab] [1,5] benzodiazepine To a stirred solution, under nitrogen, of 19.9 g of n-propylamine in 120 ml of ethanol is added in portions 12.0 g of IIB over a period of 4–5 hours. The solution is charcoaled, filtered and concentrated. The residue is dissolved in 250 ml of chloroform, washed with water, dried over $Na_2SO_4$ and concentrated in vacuo to a solid. This is boiled and triturated with 15 ml of ethyl acetate, cooled and dried to yield 6-methyl-7-n-propylaminoacetyl-1,2,6,7-tetrahydroindolo [1,7-ab] [1,5] benzodiazepine, m.p. 113°–118° C. Analysis: Calculated for $C_{21}H_{25}N_3O$: 75.19%C; 7.51%H; 12.53%N. Found: 75.38%H; 7.38%H; 12.47%N.

IIIH.
7-(N-Benzyl-N-methylaminoacetyl)-6-methyl-1,2,6,7-tetrahydroindolo [1,7-ab] [1,5] benzodiazepine A stirred mixture of 18.0 g of IIB and 18.2 g of methylbenzylamine in 150 ml of absolute ethanol is heated to 60° C. for 1 hour. The resultant solution is concentrated to an oil which is dissolved in 250 ml of methylene chloride and is extracted with water. The organic phase is then dried over $Na_2SO_4$ and concentrated to an oil. The oil is dissolved in 35 ml ether and scratched until crystals formed. After several hours, these are filtered, washed with ether and dried to afford 7-(N-benzyl-N-methylaminoacetyl)-6-methyl-1,2,6,7-tetrahydroindolo [1,7-ab] [1,5] benzodiazepine, with m.p. 101°–106° C.

Analysis: Calculated for $C_{26}H_{27}N_3O$: 78.56%C; 6.85%H; 10.57%N. Found: 78.75%C; 7.11%H; 10.29%N.

III I.
6-Methyl-7-(N-methyl-3-aminopropionyl)-1,2,6,7-tetrahydroindolo [1,7-ab] [1,5] benzodiazepine A stirred mixture of 14.9 g of IIC in 200 ml of absolute methanol is cooled to 0°–5° C. Into this is passed gaseous monomethylamine until the solvent is saturated, and at a rate as to keep the temperature below 5° C. The mixture is allowed to reach room temperature and after 2 hours a solution results. The solution is decolorized by boiling with charcoal and is then concentrated to an oil. The oil is taken up in 250 ml of chloroform and extracted with water, with 3N—NaOH, again with water, dried over $Na_2SO_4$ and concentrated to an oil which crystallizes overnight. The crystals are boiled and triturated with 50 ml of ether to afford 6-methyl-7-(N-methyl-3-aminopropionyl)-1,2,6,7-tetrahydroindolo [1,7-ab] [1,5] benzodiazepine, m.p.124°–126° C.

Analysis: Calculated for $C_{20}H_{23}N_3O$: 74.74%C; 7.21%H; 13.07%N. Found: 74.54%C; 7.18%H; 12.96%N.

IIIJ.
7-(N,N-dimethyl-3-aminopropionyl)-6-methyl-1,2,6,7-tetrahydroindolo [1,7-ab] [1,5] benzodiazepine A stirred slurry of 13.7 g of IIC in 150 ml of absolute methanol is cooled to 0°–5° C., and kept at that temperature during the slow introduction of gaseous dimethylamine. When the solvent is saturated with gas, the mixture is stirred at room temperature for 1 hour. The solution is boiled 10 minutes with charcoal, filtered and concentrated to an oil. This is dissolved in 250 ml of methylene chloride and extracted with water, 3N—NaOH, and water, dried over $Na_2SO_4$, and concentrated to an oil. The oil is digested with hexane and quickly sets solid with crystals. These are collected, washed with hexane and dried to afford 7-(N,N-dimethyl-3-aminopropionyl)-6-methyl-1,2,6,7-tetrahydroindolo [1,7-ab] [1,5] benzodiazepine, m.p. 138°–142° C.

Analysis: Calculated for $C_{21}H_{25}N_3O$: 75.19%C; 7.53%H; 12.53%N. Found: 75.43%C; 7.41%H; 12.63%N.

IIIK.
7-(N,N-Diethyl-3-aminopropionyl)-6-methyl-1,2,6,7-tetrahydroindolo [1,7-ab] [1,5] benzodiazepine To a stirred mixture of 11.1 g of IIC in 100 ml of methanol, cooled to 0° C. is added a solution of 17.5 g of diethylamine in 50 ml of methanol. The addition is at such a rate as to maintain the reaction temperature below 5° C. The mixture is then stirred at ambient temperature overnight. The resultant solution is then concentrated to a semi-solid residue. The latter is taken up in 250 ml of chloroform and extracted with water, with 3N—NaOH, again with water, dried over $Na_2SO_4$ and concentrated to an oil. This is dissolved in 70 ml of boiling hexane (charcoal), then stirred and scratched until crystals begin to form. After standing overnight at a refrigerated temperature 7(N,N-diethyl-3-aminopropionyl)-6-methyl-1,2,6,7-tetrahydroindolo [1,7-ab] [1,5] benzodiazepine is obtained.

Analysis: Calculated for $C_{23}H_{29}N_3O$: 76.00%C; 8.04%H; 11.56%N. Found: 76.28%C; 8.08%H; 11.73%N.

IIIL.
6-Methyl-7-(3-piperidinopropionyl)-1,2,6,7-tetrahydroindolo [1,7-ab] [1,5] benzodiazepine A stirred solution, under nitrogen, of 27.2 g of piperidine in 150 ml of methanol is cooled to 0° C. and 14.8 g of IIC is added in small portions. After 2 hours at 0° C., and during the ambient warm-up to room temperature (2 hours) a solution results. This is concentrated to an oil which is taken up in 250 ml of methylene chloride. The organic solution is washed with water, with 3N—NaOH, again with water, then dried over $Na_2SO_4$ and concentrated to a thick oil. This is dissolved in 60 ml of heptane bath, then allowed to cool slowly with stirring to afford 6-methyl-7-(3-piperidinopropionyl)-1,2,6,7-tetrahydroindolo [1,7-ab] [1,5] benzodiazepine, m.p., 97°–99° C.

Analysis: Calculated for $C_{24}H_{29}N_3O$: 76.76%C; 7.78%H; 11.19%N. Found: 76.71%C; 7.86%H; 11.25%N.

In a similar manner can be prepared 6-methyl-7-(3-pyrrolidinopropionyl)-1,2,6,7-tetrahydroindolo[1,7-a,b][1,5]benzodiazepine and 6-methyl-7-(3-morpholinopropionyl)-1,2,6,7-tetrahydroindolo[1,7-a,b][1,5]benzodiazepine.

IIIM.
6-Methyl-7-[3-(4-phenylpiperazin-1-yl)propionyl]-1,2,6,7-tetrahydroindolo [1,7-ab] [1,5] benzodiazepine A stirred solution, under nitrogen, of 19.5 g of N-phenylpiperazine in 100 ml of methanol is cooled to 0°–5° C. To this is added, in portions over 1 hour, 11.1 g of IIC. The mixture is stirred at 0° C. for 2 hours more, then at ambient temperature 18 hours. The resulting solution is boiled with charcoal, filtered, and concentrated, and the residue partitioned between chloroform and water. The organic layer is washed with 3N—NaOH, with water, dried over Na$_2$SO$_4$ and then concentrated in vacuo at 100° C. to an oil which partially crystallizes. This material is digested with 100 ml of isopropyl ether, then filtered to afford 6-methyl-7-[3-(4-phenylpiperazin-1-yl)propionyl]-1,2,6,7-tetrahydroindolo [1,7-ab] [1,5] benzodiazepine, m.p. 139°–141° C.

Analysis: Calculated for C$_{29}$H$_{32}$N$_4$O: 76.96%C; 7.13%H; 12.38%N. Found: 76.76%C; 7.11%H; 12.47%N.

IIIN.
6-Methyl-7-(N,N-dimethyl-4-aminobutyryl)-1,2,6,7-tetrahydroindolo [1,7-ab] [1,5] benzodiazepine hydrochloride.

Into a stirred mixture of 14.4 g of IIE in 150 ml of ethanol is passed gaseous dimethylamine until the solvent is saturated. Sodium iodide (1.4 g) is added and the mixture is refluxed for 4 days. The solvent is then removed under reduced pressure and the residue is partitioned between chloroform and water. The organic phase is extracted further with water, with 3N—NaOH, once more with water, then dried over Na$_2$SO$_4$ and concentrated in vacuo to an oily crystalline mass. This material is dissolved in a minimal volume of chloroform and absorbed on a column containing 600 g of silica gel made up in toluene. Elution first with toluene, then with chloroform in toluene, and then with methanol in chloroform gives fractions containing purified product. These are combined and concentrated to afford an oil which crystallizes. For salt formation, a portion of the oil is dissolved in 20 ml of ethanol and the well-stirred solution is treated with 60 ml of ethereal HCl. The crystalline salt is filtered, washed well with ether, and dried to yield 6-methyl-7-(N,N-dimethyl-4-aminobutyryl)-1,2,6,7-tetrahydroindolo [1,7-ab] [1,5] benzodiazepine hydrochloride, m.p. 226°–228° C.

Analysis: Calculated for C$_{22}$H$_{27}$N$_3$O.HCl: 68.47%C; 7.31%H; 10.89%N. Found: 68.37%C; 7.09%H; 10.75%N.

IIIO.
6-Methyl-7-(N-propyl-3-aminopropionyl)-1,2,6,7-tetrahydroindolo [1,7-ab] [1,5] benzodiazepine hydrochloride To a stirred solution of 19.9 g of n-propylamine in 120 ml of absolute ethanol is added 12.5 g of IIC in portions. When the addition is complete the solution is stirred for one hour and then the solution is concentrated. The resultant residue is partitioned between methylene chloride and water. The organic phase is separated and washed further with dilute NaOH, again with water, dried over Na$_2$SO$_4$ and concentrated in vacuo to an oil. This material is dissolved in 25 ml of chloroform and column chromatographed by passage through a column containing silica gel made up in toluene. The resultant product is dissolved in ethanol and treated with ethereal hydrogen chloride to yield 6-methyl-7-(N-propyl-3-aminopropionyl)-1,2,6,7-tetrahydroindolo [1,7-ab] [1,5] benzodiazepine hydrochloride, m.p. 186°–190° C.

Analysis: Calculated for C$_{22}$H$_{27}$N$_3$O.HCl: 68.47%C; 7.31%H; 10.89%N. Found: 68.29%C; 7.41%H; 10.82%N.

EXAMPLE IV

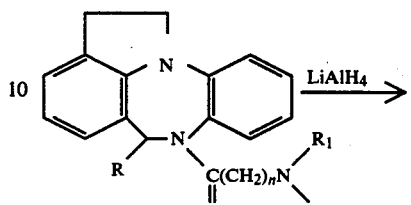

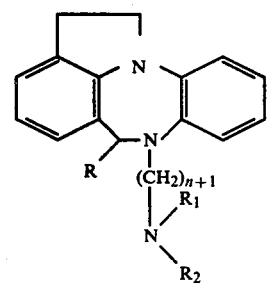

IV A.
7-(N,N-Dimethyl-2-aminoethyl)-6-methyl-1,2,6,7-tetrahydroindolo [1,7-ab] [1,5] benzodiazepine hydrobromide To 200 ml of dry tetrahydrofuran, stirred and cooled to 0° C. under nitrogen, is added 2.28 g of lithium aluminum hydride in several portions. This mixture is then treated dropwise with a solution of 9.64 g of IIIF in 50 ml of dry tetrahydrofuran over 1.0 hour. The reaction mixture is stirred and refluxed 18 hours, then cooled to 0°–5° C. and treated with a solution of 25 ml water in 25 ml tetrahydrofuran (2 hours) while maintaining the temperature below 5° C. Then 25 ml more water is added and the mixture is stirred at ambient temperature for 2 hours, filtered, and the cake washed with tetrahydrofuran. The combined filtrates are concentrated, taken up in 300 ml of ether and the organic phase is extracted twice with water, dried over Na$_2$SO$_4$, boiled with charcoal, filtered and concentrated to give an oil. This oil is dissolved in 25 ml of ethanol and treated dropwise with 25 ml of ether previously saturated with HBr gas. After 3 hours the solution sets solid with crystals which are collected, washed well with ether and dried to yield 7-(N,N-dimethyl-2-aminoethyl)-6-methyl-1,2,6,7-tetrahydroindolo [1,7-ab] [1,5] benzodiazepine hydrobromide, m.p. 225°–227° C.

Analysis: Calculated for C$_{20}$H$_{25}$N$_3$.HBr: 61.86%C; 6.75%H; 10.82%N. Found: 61.97%C; 6.83%H; 10.71%N.

IV B.
7-(N-Benzyl-N-methyl-2-aminoethyl)-6-methyl-1,2,6,7-tetrahydroindolo [1,7-ab] [1,5] benzodiazepine dihydrobromide To 200 ml of dry tetrahydrofuran, cooled to 0° C. and stirred under nitrogen, is added 3.0 g of lithium aluminum hydride in portions over 0.5 hours. Then 8.50 g of IIIH is added in portions over a 15 minute period. The mixture is allowed to warm to room temperature and then it is refluxed 18 hours. After cooling to 0°–5° C., a solution of 25 ml water in 25 ml THF is cautiously added dropwise, while maintaining the temperature below 10° C. When the addition is complete, the mixture is stirred 2 hours more at ambient temperature, then filtered, the cake is washed with THF and the filtrate concentrated to an oil. This is dissolved in 20 ml of ethanol, cooled to 0° C., and the solution saturated by a slow stream of HBr gas to crystallize a salt. The salt is filtered, washed with ether, and dried to afford 7-(N-Benzyl-N-methyl-2-aminoethyl)-6-methyl-1,2,6,7-tetrahydroindolo [1,7-ab] [1,5] benzodiazepine dihydrobromide, m.p. 157°–160° C. (dec.).

Analysis: Calculated for $C_{26}H_{29}N_3.2HBr$: 56.26%C; 5.73%H; 7.70%N. Found: 56.92%C; 6.03%H; 7.17%N.

IV C.

6-Methyl-7-(N-propyl-2-aminoethyl)-1,2,6,7-tetrahydroindolo [1,7-ab] [1,5] benzodiazepine dihydrobromide To a stirred mixture of 1.40 g of lithium aluminum hydride in 100 ml of dry tetrahydrofuran (THF), kept at 0°–5° C. under nitrogen, is added dropwise a solution of 6.20 g of IIIG in 50 ml of THF. When the addition is complete (1 hour), the mixture is stirred in the cold for one hour, at ambient temperature for 1 hour, then refluxed for 5 hours. After cooling below 5° C., the reaction mixture is quenched by cautious and slow addition of a solution of 25 ml water in 25 ml of THF. The resulting mixture is stirred for 1 hour at room temperature and then filtered. The filtrate is concentrated and the residue is partitioned between dichloromethane and water. The organic phase is washed with water, then dried over $Na_2SO_4$ and concentrated to an oil which sets solid with crystals. This material is dissolved in 25 ml of methanol, cooled and treated with gaseous hydrogen bromide to form the dihydrobromide salt. Then 100 ml of ether is added to complete precipitation of 6-methyl-7-(N-propyl-2-aminoethyl)-1,2,6,7-tetrahydroindolo [1,7-ab] [1,5] benzodiazepine dihydrobromide, m.p. 230°–232° C. (dec.).

Analysis: Calculated for $C_{21}H_{27}N_3.2HBr$: 52.19%C; 6.05%H; 8.69%N. Found: 51.93%C; 5.81%H; 8.37%N.

EXAMPLE V

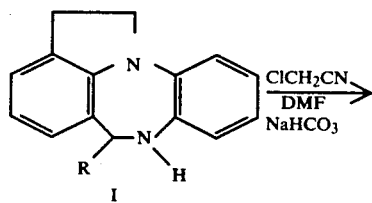

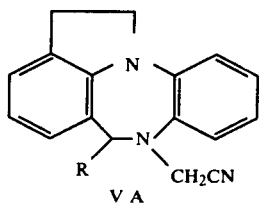

V A

1. LiAlH$_4$
2. HBr

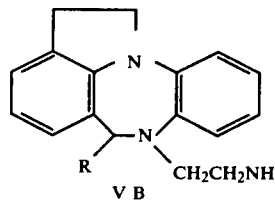

V B

V A. 6-Methyl-1,2,6,7-tetrahydroindolo [1,7-ab] [1,5] benzodiazepin-7-ylacetonitrile A stirred mixture of 23.6 g of IB, 15.1 g of chloroacetonitrile, and 16.8 g of sodium bicarbonate in 200 ml of DMF is heated at 75° C. under nitrogen 18 hours. Then the reaction mixture is cooled to room temperature and 200 ml of water is added dropwise over 1 hour with vigorous stirring. After an additional hour, a crystalline product is filtered, washed with water, then dried to yield 6-methyl-1,2,6,7-tetrahydroindolo [1,7-ab] [1,5] benzodiazepin-7-ylacetonitrile, m.p. 148°–150° C.

V B.

7-(2-Aminoethyl)-6-methyl-1,2,6,7-tetrahydroindolo [1,7-ab] [1,5] benzodiazepine dihydrobromide To a stirred mixture under nitrogen of 4.56 g of lithium aluminum hydride in 50 ml of dry tetrahydrofuran is added a solution of 8.26 g of V A in 90 ml dry THF. When the addition is complete (1 hour), the mixture is stirred 1 hour at room temperature, refluxed for 5 hours, then left 18 hours at ambient temperature. A solution of 25 ml water in 25 ml THF is added (3 hours) keeping the temperature below 10° C. After stirring an additional 2 hours, the salts are filtered, washed with THF, and discarded. The combined filtrates are concentrated to a residue which is taken up in methylene chloride. This is extracted with water, dried over $Na_2SO_4$ and concentrated to an oil which crystallizes. This is dissolved in 50 ml of ethanol, cooled to 0° C., the gaseous HBr is slowly passed into the solution until it is saturated. The crystals which separate are filtered, washed with ether, and dried to afford 7-(2-aminoethyl)-6-methyl-1,2,6,7-tetrahydroindolo[1,7-ab] [1,5] benzodiazepine dihydrobromide, m.p. 237°–240° C. (dec.).

Analysis: Calculated for $C_{18}H_{21}N_3.2HBr$: 49.00%C; 5.25%H; 9.52%N. Found: 48.86%C; 4.97%H; 9.47%N.

EXAMPLE VI

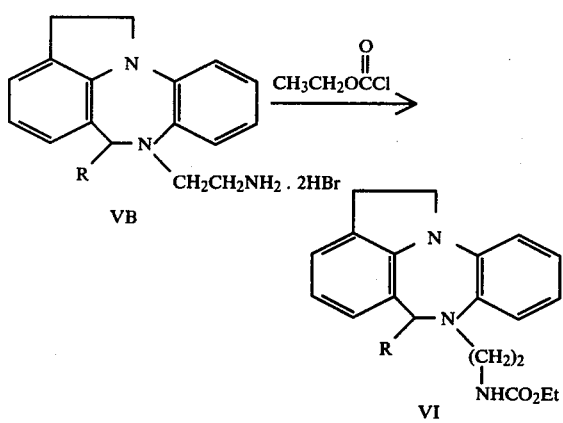

6-Methyl-7-(N-ethoxycarbonyl-2-aminoethyl)-1,2,6,7-tetrahydroindolo [1,7-ab] [1,5] benzodiazepine A stirred mixture of 14.0 g of VB and 10.8 g of sodium bicarbonate in 140 ml of methylene chloride is cooled to 0°–5° C. under nitrogen and then treated dropwise with a solution of 5.20 g of ethyl chloroformate in 50 ml of methylene chloride. When the addition is complete (1 hour), the mixture is stirred 18 hours at ambient temperature and water is added to dissolve the salts. The organic phase is separated, washed with water, dried over $Na_2SO_4$, and concentrated in vacuo to an oil. This is dissolved in 10 ml hot methanol to afford, after cooling, 6-methyl-7-(N-ethoxycarbonyl-2-aminoethyl)-1,2,6,7-tetrahydroindolo [1,7-ab] [1,5] benzodiazepine, m.p. 94°–96° C.

Analysis: Calculated for $C_{21}H_{25}N_3O$: 71.77%C; 7.17%H; 11.96%N. Found: 71.51%C; 7.17%H; 12.04%N.

EXAMPLE VII

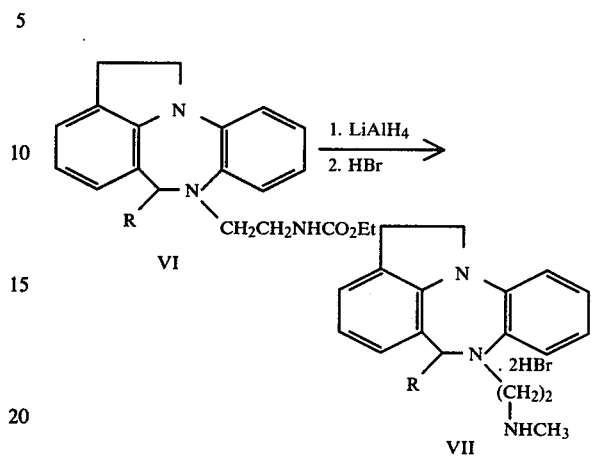

6-Methyl-7-(N-methyl-2-aminoethyl)-1,2,6,7-tetrahydroindolo [1,7-ab] [1,5] benzodiazepine dihydrobromide To a stirred mixture of 3.42 g of lithium aluminum hydride in 100 ml of dry THF, kept at 0°–5° C. under nitrogen, is added a solution of 8.0 g of VI in 50 ml of THF. When the addition is complete (1 hour), the mixture is stirred 1 hour longer at 0° C., 1 hour at ambient temperature, and refluxed 18 hours. The mixture is then cooled below 5° C. and is quenched by the cautious addition of 25 ml water in 25 ml THF. The salts are removed by filtration and the filtrate is concentrated. The residue is partitioned between chloroform and water, the organic phase is separated, extracted with water, dried over $Na_2SO_4$, and finally concentrated in vacuo to an oil. The oil is dissolved in 25 ml methanol, and the stirred solution is treated in one portion with 100 ml of ether previously saturated with HBr gas. The crystalline salt which separates is filtered, washed well with ether, and dried to afford 6-methyl-7-(N-methyl-2-aminoethyl)-1,2,6,7-tetrahydroindolo [1,7-ab] [1,5] benzodiazepine dihydrobromide, m.p. 241°–243° C. (dec.).

Analysis: Calculated for $C_{19}H_{23}N_3.2HBr$: 50.13%C; 5.54%H; 9.23%N. Found: 49.67%C; 5.40%H; 9.16%N.

EXAMPLE VIII

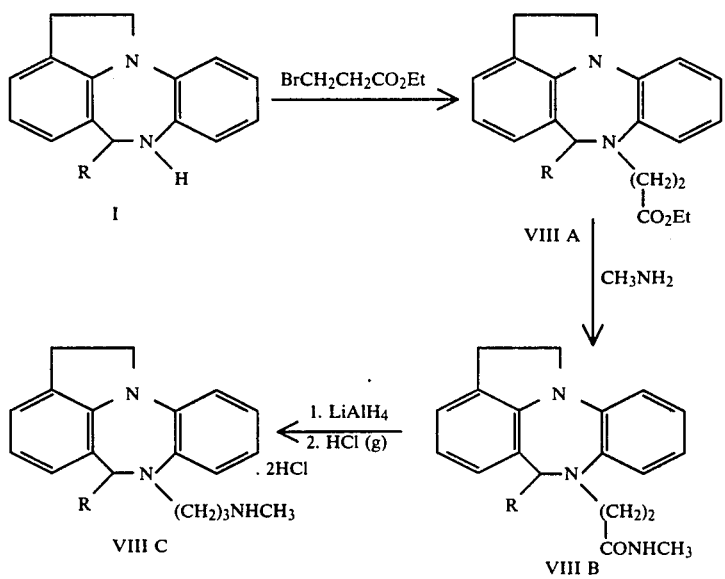

VIII A. Ethyl-3-(6-methyl-1,2,6,7-tetrahydroindolo [1,7-ab] [1,5] benzodiazepin-7-yl) propionate A stirred mixture, under nitrogen, of 2.36 g of IB, 1.68 g of powdered sodium bicarbonate and 3.62 g of ethyl bromopropionate in 50 ml of acetone is refluxed for 3 days. The mixture is then concentrated to a moist residue which is partitioned between methylene chloride and water. The organic phase is extracted with water, then dried over $Na_2SO_4$ and concentrated in vacuo to an oil. This material is absorbed on a chromatography column containing 100 g of silica gel made up in benzene. After several liters of benzene are eluted, fractions containing pure product are obtained. They are combined and concentrated to an oil which crystallizes to yield ethyl-3-(6-methyl-1,2,6,7-tetrahydroindolo [1,7-ab] [1,5] benzodiazepin-7-yl) propionate, m.p. 96°–98° C.

VIII B. N-Methyl-3-(6-methyl-1,2,6,7-tetrahydroindolo [1,7-ab] [1,5] benzodiazepin-7-yl) propionamide A stirred mixture of 26.0 g of VIII A in 500 ml absolute ethanol is cooled to 0° C. and kept below 5° C. while gaseous methylamine is passed through. When the solvent is fully saturated with the amine, the resulting solution is stirred at ambient temperature for 24 hours, then refluxed for 24 hours. The solution is concentrated in vacuo to an oil. This material is dissolved in 100 ml chloroform and absorbed on a column containing 650 g silica gel made up in toluene. Elution is carried out first with toluene, then $CHCl_3$ in toluene, then $CHCl_3$ to yield N-methyl-3-(6-methyl-1,2,6,7-tetrahydroindolo [1,7-ab] [1,5] benzodiazepin-7-yl) propionamide, m.p. 143°–145° C.

Analysis: Calculated for $C_{20}H_{23}N_3O$: 74.74%C; 7.21%H; 13.07%N. Found: 74.73%C; 7.32%H; 13.34%N.

VIII C. 6-Methyl-7-(N-methyl-3-aminopropyl)-1,2,6,7-tetrahydroindolo [1,7-ab] [1,5] benzodiazepine dihydrochloride To a stirred mixture of 3.95 g of lithium aluminum hydride in 100 ml of dry THF, kept at 0°–5° C. under $N_2$, is added dropwise a solution of 8.60 g of VIII B in 100 ml of dry THF. When the addition is complete (1 hour), the mixture is stirred for 2 hours at room temperature, then refluxed 18 hours. After cooling to 0° C., the reaction mixture is quenched by cautious and slow addition of a solution of 25 ml water in 25 ml of THF. The resulting mixture is stirred 1 hour at room temperature and then filtered. The filtrate is concentrated to an oily residue which is partitioned between methylene chloride and water. The organic phase is washed with water, then dried over $Na_2SO_4$ and concentrated in vacuo to an oil. A portion of the oil is dissolved in 45 ml of ethanol, and with good stirring, ether saturated with gaseous HCl is added to crystallize out 6-methyl-7-(n-methyl-3-aminopropyl)-1,2,6,7-tetrahydroindolo [1,7-ab] [1,5] benzodiazepine dihydrochloride, m.p. 237°–239° C. (dec.).

Analysis: Calculated for $C_{20}H_{25}N_3 \cdot 2HCl$: 63.16%C; 7.15%H; 11.05%N. Found: 63.03%C; 7.14%H; 10.90%N.

EXAMPLE IX

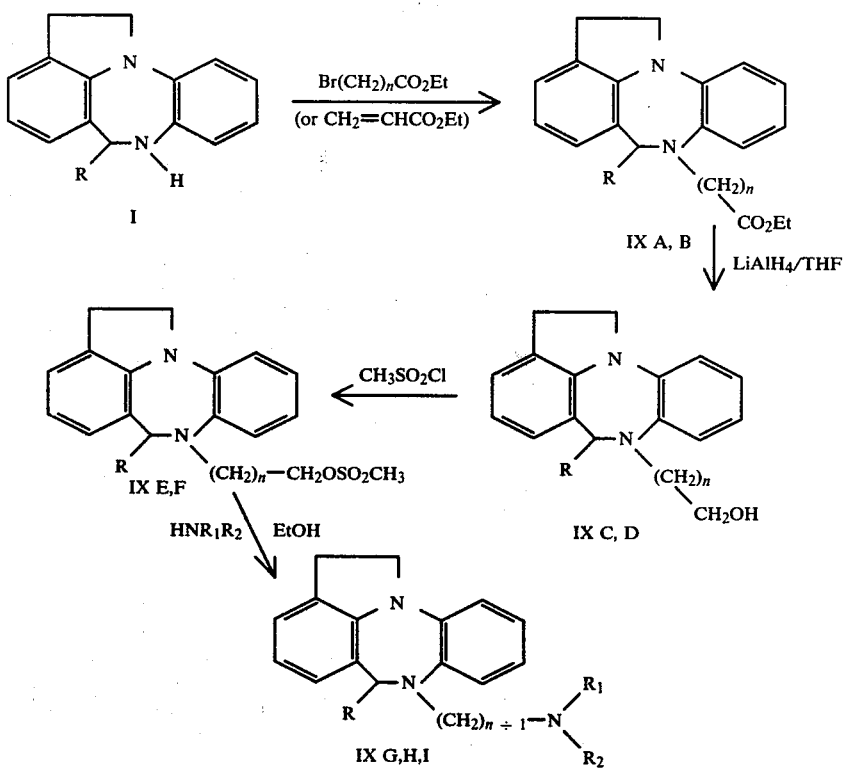

IX A. Ethyl-3-(1,2,6,7-tetrahydroindolo [1,7-ab] [1,5] benzodiazepin-7-yl) acetate To a stirred slurry of 11.1 g of IA and 4.2 g of sodium bicarbonate in 100 ml DMF at room temperature under nitrogen is added dropwise 6.1 ml of ethyl bromoacetate. When the addition is complete, the mixture is placed in a preheated bath (35° C.) where the temperature is allowed to rise gradually to 94° C. (1.1 hours). The solution is concentrated and partitioned between chloroform and water. The organic phase is washed with water and brine, dried over sodium sulfate, filtered, and concentrated to yield ethyl-3-(1,2,6,7-tetrahydroindolo [1,7-ab] [1,5] benzodiazepin-7-yl) acetate.

IX B. Ethyl-3-(1,2,6,7-tetrahydroindolo [1,7-ab] [1,5] benzodiazepin-7-yl) propionate A mixture of 12.9 g of IA, 11.5 ml of ethylacrylate, and 1.2 ml of glacial acetic acid is slowly heated to reflux. While heating the mixture, 21.5 ml of ethyl acrylate and 1.2 ml of glacial acetic acid are added to form a homogeneous solution which is refluxed 18 hours. After concentration the residue is dissolved in chloroform, then washed with water, saturated sodium bicarbonate solution, water and brine, dried over sodium sulfate, filtered, and concentrated to yield Ethyl-3-(1,2,6,7-tetrahydroindolo [1,7-ab] [1,5] benzodiazepin-7-yl) propionate.

IX C. 2-(1,2,6,7-Tetrahydroindolo [1,7-ab] [1,5] benzodiazepin-7-yl)ethanol

To a mixture of 0.98 g LiAlH$_4$ in 100 ml cold ($-3°$ C.) THF under nitrogen is added dropwise a solution of 10.6 g of the ester IX A in 70 ml THF. This is slowly heated and allowed to reflux for about 4.5 hours, then permitted to stand at room temperature for three days. After cooling to 5°–10° C., the product is treated with 1 ml water, 2 ml 10% NaOH and 2 ml water, and filtered. The aluminum salts are washed with hot chloroform and the combined filtrates are washed with brine, dried over sodium sulfate, and concentrated to yield 2-(1,2,6,7-Tetrahydroindolo [1,7-ab] [1,5] benzodiazepin-7-yl)ethanol.

IX D. 3-(1,2,6,7-tetrahydroindolo [1,7-ab] [1,5] benzodiazepin-7-yl)-1-propanol

A mixture of 0.12 g LiAlH$_4$ and 1.62 g of the ester IX B in 12 ml dry THF are heated at reflux for 3.5 hours, then cooled. The ice cold product is treated with 1 ml 10% NaOH, 1 ml water, and filtered. The aluminum salts are washed with hot CHCl$_3$ and the combined filtrates are washed twice with brine, dried over Na$_2$SO$_4$ and concentrated to yield 3-(1,2,6,7-tetrahydroindolo [1,7-ab] [1,5] benzodiazepin-7-yl)-1-propanol.

Conversion to the HCl salt (ethereal HCl) and recrystallization from methanol-ether afforded pure material, m.p. 193.5–196° C.

IX E. 2-(1,2,6,7-tetrahydroindolo [1,7-ab] [1,5] benzodiazepin-7-yl)-ethyl methanesulfonate To a cold (0° C.), stirred solution of 8.1 g alcohol IX C in 70 ml methylene chloride, kept under nitrogen, is added 6.4 ml triethylamine, then 2.83 ml methanesulfonyl chloride dropwise. About 27 minutes after the addition the product is washed with cold water, and then with cold 2 N—HCl. The organic phase is washed with saturated sodium bicarbonate solution, dried over sodium sulfate, and concentrated to yield 2-(1,2,6,7-tetrahydroindolo [1,7-ab] [1,5] benzodiazepin-7-yl)-ethyl methanesulfonate.

IX F. 3-(1,2,6,7-tetrhydroindolo [1,7-ab] [1,5] benzodiazepin-7-yl)-propyl methanesulfonate To a cold (0°–5° C.), stirred solution of 9.7 g alcohol IX D and 7.3 ml triethylamine in 70 ml methylene chloride, kept under nitrogen, is added dropwise 3.2 ml of methanesulfonyl chloride. About 15 minutes after the addition the product is washed with cold water, cold 2 N-HCl, saturated sodium bicarbonate solution, and brine, dried over sodium sulfate, and concentrated to yield 3-(1,2,6,7-tetrhydroindolo [1,7-ab] [1,5] benzodiazepin-7-yl)propyl methanesulfonate.

IX G.
7-(N-Methyl-2-aminoethyl)-1,2,6,7-tetrahydroindolo [1,7-ab] [1,5] benzodiazepine oxalate A solution of 8.8 g of mesylate IX E in 150 ml absolute ethanol is heated at reflux for 1 hour while bubbling in methylamine gas. The resulting product is concentrated to an oil, dissolved in methylene chloride and washed with 4 N-NaOH, with water and with brine, dried over $Na_2SO_4$, and concentrated to give an oil (free base).

A solution of 2.5 g of the free base in 30 ml warm ethanol is added in one portion to a stirred solution of 0.81 g oxalic acid in 100 ml dry ether. The resulting solid is filtered, washed with dry ether and dried at 60° C. under vacuum to give 7-(N-methyl-2-aminoethyl)-1,2,6,7-tetrahydroindolo [1,7-ab] [1,5] benzodiazepine oxalate, m.p. 180.5° C. (dec.).

Analysis: Calculated for $C_{18}H_{21}N_3 \cdot C_2H_2O_4$: 65.03%C; 6.28%H; 11.37%N. Found: 65.69%C; 6.12%H; 11.47%N.

IX H.
7-(N-Methyl-3-aminopropyl)-1,2,6,7-tetrahydroindolo [1,7-ab] [1,5] benzodiazepine dihydrobromide A solution of 6.2 g of the mesylate IX F in 150 ml absolute ethanol is heated at reflux for 70 min. while bubbling in gaseous monomethylamine. The resulting product is concentrated, dissolved in chloroform, washed with 5% NaOH, water and brine, dried ($Na_2SO_4$) and concentrated to give a crude amine.

Salt formation (EtOH/ethereal HBr) and recrystallization from ethanol-ether affords 7-(N-methyl-3-aminopropyl)-1,2,6,7-tetrahydroindolo [1,7-ab] [1,5] benzodiazepine dihydrobromide, m.p. 217.5° C. (dec.).

Analysis: Calculated for $C_{19}H_{23}N_3 \cdot 2HBr$: 50.13%C; 5.54%H; 9.23%N. Found: 50.27%C; 5.50%H; 8.82%N.

IX I.
7-(N,N-Dimethyl-3-aminopropyl)-1,2,6,7-tetrahydroindolo [1,7-ab] [1,5] benzodiazepine dihydrochloride A stirred suspension of 5.7 g of mesylate IX G in 150 ml absolute ethanol is heated at reflux for 30 minutes while bubbling in gaseous dimethylamine. The resulting solution is concentrated and the residue is dissolved in chloroform, washed with water, 5% aqueous NaOH and brine, dried ($Na_2SO_4$) and concentrated to give a crude amine.

Conversion to the salt (ethanol/ethereal HCl) and recrystallization from $CH_3CN$-EtOAc affords 7-(N,N-dimethyl-3-aminopropyl)-1,2,6,7-tetradhydroindolo [1,7-ab] [1,5] benzodiazepine dihydrochloride, m.p. 199°–202° C.

Analysis: Calculated for $C_{20}H_{25}N_3 \cdot 2HCl$: 63.16%C; 7.16%H; 11.05%N. Found: 63.44%C; 6.91%H; 11.53%N.

We claim:
1. A compound of the formula:

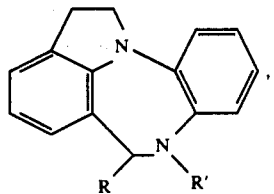

or a pharmaceutically acceptable acid addition salt thereof wherein
R is hydrogen, loweralkyl, or cycloalkyl;
R' is

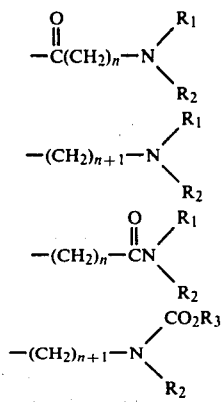

n is an integer from 1 to 3;
$R_1$ taken alone is hydrogen, loweralkyl or phenylloweralkyl;
$R_2$ taken alone is hydrogen or loweralkyl;
or $R_1$ and $R_2$, taken together with the nitrogen to which they are attached, are pyrrolidinyl, piperidino, morpholino or phenylpiperazinyl; and
$R_3$ is loweralkyl.

2. A compound as defined in claim 1 which is 7-methylaminoacetyl-1,2,6,7-tetrahydroindolo[1,7-ab][1,5]benzodiazepine or a salt thereof.

3. A compound as defined in claim 1 which is 7-dimethylaminoacetyl-1,2,6,7-tetrahydroindolo[1,7-ab][1,5]benzodiazepine or a salt thereof.

4. A compound as defined in claim 1 which is 7-(N,N-dimethyl-3-aminopropionyl)-1,2,6,7-tetrahydroindolo[1,7-ab][1,5]benzodiazepine or a salt thereof.

5. A compound as defined in claim 1 which is 6-cyclohexyl-7-(N,N-dimethyl-3-aminopropionyl)-1,2,6,7-tetrahydroindolo[1,7-ab][1,5]benzodiazepine or a salt thereof.

6. A compound as defined in claim 1 which is 6-methyl-7-methylaminoacetyl-1,2,6,7-tetrahydroindolo[1,7-ab][1,5]benzodiazepine or a salt thereof.

7. A compound as defined in claim 1 which is 7-dimethylaminoacetyl-6-methyl-1,2,6,7-tetrahydroindolo[1,7-ab][1,5]benzodiazepine or a salt thereof.

8. A compound as defined in claim 1 which is 6-methyl-7-n-propylaminoacetyl-1,2,6,7-tetrahydroindolo[1,7-ab][1,5]benzodiazepine or a salt thereof.

9. A compound as defined in claim 1 which is 7-(N-benzyl-N-methylaminoacetyl)-6-methyl-1,2,6,7-tetrahydroindolo[1,7-ab][1,5]benzodiazepine or a salt thereof.

10. A compound as defined in claim 1 which is 6-methyl-7-(N-methyl-3-aminopropionyl)-1,2,6,7-tetrahydroindolo[1,7-ab][1,5]benzodiazepine or a salt thereof.

11. A compound as defined in claim 1 which is 7-(N,N-dimethyl-3-aminopropionyl)-6-methyl-1,2,6,7-tetrahydroindolo[1,7-ab][1,5]benzodiazepine or a salt thereof.

12. A compound as defined in claim 1 which is 7-(N,N-diethyl-3-aminopropionyl)-6-methyl-1,2,6,7-tetrahydroindolo[1,7-ab][1,5]benzodiazepine or a salt thereof.

13. A compound as defined in claim 1 which is 6-methyl-7-(3-piperidinopropionyl)-1,2,6,7-tetrahydroindolo[1,7-ab][1,5]benzodiazepine or a salt thereof.

14. A compound as defined in claim 1 which is 6-methyl-7-[3-(4-phenylpiperazin-1-yl)propionyl]-1,2,6,7-tetrahydroindolo[1,7-ab][1,5]benzodiazepine or a salt thereof.

15. A compound as defined in claim 1 which is 6-methyl-7-(N,N-dimethyl-4-aminobutyryl)-1,2,6,7-tetrahydroindolo[1,7-ab][1,5]benzodiazepine or a salt thereof.

16. A compound as defined in claim 1 which is 6-methyl-7-(N-propyl-3-aminopropionyl)-1,2,6,7-tetrahydroindolo[1,7-ab][1,5]benzodiazepine or a salt thereof.

17. A compound as defined in claim 1 which is 7-(N,N-dimethyl-2-aminoethyl)-6-methyl-1,2,6,7-tetrahydroindolo[1,7-ab][1,5]benzodiazepine or a salt thereof.

18. A compound as defined in claim 1 which is 7-(N-benzyl-N-methyl-2-aminoethyl)-6-methyl-1,2,6,7-tetrahydroindolo[1,7-ab][1,5]benzodiazepine or a salt thereof.

19. A compound as defined in claim 1 which is 6-methyl-7-(N-propyl-2-aminomethyl)-1,2,6,7-tetrahydroindolo[1,7-ab][1,5]benzodiazepine or a salt thereof.

20. A compound as defined in claim 1 which is 7-(2-aminoethyl)-6-methyl-1,2,6,7-tetrahydroindolo[1,7-ab][1,5]benzodiazepine or a salt thereof.

21. A compound as defined in claim 1 which is 6-methyl-7-(N-ethoxycarbonyl-2-aminoethyl)-1,2,6,7-tetrahydroindolo[1,7-ab][1,5]benzodiazepine or a salt thereof.

22. A compound as defined in claim 1 which is 6-methyl-7-(N-methyl-2-aminoethyl)-1,2,6,7-tetrahydroindolo[1,7-ab][1,5]benzodiazepine or a salt thereof.

23. A compound as defined in claim 1 which is N-methyl-3-(6-methyl-1,2,6,7-tetrahydroindolo[1,7-ab][1,5]benzodiazepine-7-yl)propanamide or a salt thereof.

24. A compound as defined in claim 1 which is 7-(N-methyl-2-aminoethyl)-1,2,6,7-tetrahydroindolo[1,7-ab][1,5]benzodiazepine or a salt thereof.

25. A compound as defined in claim 1 which is 7-(N-methyl-3-aminopropyl)-1,2,6,7-tetrahydroindolo[1,7-ab][1,5]benzodiazepine or a salt thereof.

26. A compound as defined in claim 1 which is 6-methyl-7-(N-methyl-3-aminopropyl)-1,2,6,7-tetrahydroindolo[1,7-ab][1,5]benzodiazepine or a salt thereof.

27. A compound as defined in claim 1 which is 7-(N,N-dimethyl-3-aminopropyl)-1,2,6,7-tetrahydroindolo[1,7-ab][1,5]benzodiazepine or a salt thereof.

28. A method of treating depression which comprises administering to a patient in need thereof a pharmaceutically effective amount of a compound defined in claim 1.

29. A method of treating inflammation which comprises administering to a patient in need thereof a pharmaceutically effective amount of a compound defined in claim 1.

30. A method of treating pain which comprises administering to a patient in need thereof a pharmaceutically effective amount of a compound defined in claim 1.

31. A pharmaceutical composition for the treatment of inflammation, pain or depression which comprises between about 0.5 and about 70% by weight of a compound defined in claim 1 and a pharmaceutically acceptable carrier therefor.

* * * * *